(12) United States Patent
Stelter et al.

(10) Patent No.: US 8,409,280 B2
(45) Date of Patent: Apr. 2, 2013

(54) BREAST PROSTHESIS

(75) Inventors: Nils Stelter, Frasdorf (DE); Michaela Reusch, Freilassing (DE); Florian Leinenbach, Kolbermoor (DE); Brigitte Seehaus, Halfing (DE)

(73) Assignee: Amoena Medizin-Orthopaedie-Technik GmbH, Raubling (DE)

( * ) Notice: Subject to any disclaimer, the term of this patent is extended or adjusted under 35 U.S.C. 154(b) by 58 days.

(21) Appl. No.: 12/888,722

(22) Filed: Sep. 23, 2010

(65) Prior Publication Data

US 2011/0245921 A1 Oct. 6, 2011

(30) Foreign Application Priority Data

Sep. 23, 2009 (DE) .......................... 10 2009 042 713

(51) Int. Cl.
*A61F 2/12* (2006.01)
(52) U.S. Cl. ........................................................... 623/8
(58) Field of Classification Search .................. 623/7–8; 450/57

See application file for complete search history.

(56) References Cited

U.S. PATENT DOCUMENTS

| 3,067,431 | A | * | 12/1962 | Kausch | 623/7 |
| 3,366,975 | A | * | 2/1968 | Pangman | 623/8 |
| 4,024,876 | A | * | 5/1977 | Penrock | 450/48 |
| 4,086,666 | A | * | 5/1978 | Vaskys et al. | 623/7 |
| 5,940,888 | A | * | 8/1999 | Sher | 2/267 |
| 6,679,912 | B2 | * | 1/2004 | Stelter | 623/7 |
| 7,959,488 | B2 | * | 6/2011 | Talamo | 450/57 |
| 2002/0103539 | A1 | * | 8/2002 | Stelter | 623/7 |
| 2006/0025859 | A1 | * | 2/2006 | Stelter et al. | 623/7 |
| 2006/0265060 | A1 | | 11/2006 | Stelter et al. | |
| 2009/0276043 | A1 | * | 11/2009 | Bowman et al. | 623/7 |
| 2010/0222880 | A1 | * | 9/2010 | Muscat et al. | 623/7 |
| 2010/0298934 | A1 | * | 11/2010 | Stelter | 623/7 |

FOREIGN PATENT DOCUMENTS

| DE | 7440175 | 5/1975 |
| DE | 9210758 | 10/1992 |
| DE | 29712015 | 11/1998 |
| DE | 202004003278 | 5/2004 |
| DE | 202004011988 | 12/2005 |
| DE | 202005007677 | 9/2006 |
| FR | 2757043 | 6/1998 |

OTHER PUBLICATIONS

Amoena life brochure issued Mar. 1, 2006, p. 19.
Anita Dialog brochure issued Apr. 4, 2006, p. 8.

* cited by examiner

*Primary Examiner* — Suzette J Gherbi
(74) *Attorney, Agent, or Firm* — Dilworth & Barrese, LLP.

(57) ABSTRACT

The present invention relates to a breast prosthesis having at least one contact surface which is intended for contact on a body surface, with the contact surface having at least one means by means of which air circulation and/or an exchange of air can be achieved between the contact surface and the body surface.

19 Claims, 4 Drawing Sheets

BREAST PROSTHESIS

BACKGROUND OF THE INVENTION

The present invention relates to a breast prosthesis having at least one contact surface which is intended for contact on a body surface.

Breast prostheses for the care of patients after breast surgery, in particular after breast amputations, are already known. Such breast prostheses are usually placed directly onto the body surface and remain there over a fairly long time period in some cases, in particular over the whole day.

Problems with respect to comfort in wear can result due to the direct contact on the body surface. It is in particular possible that perspiration occurs or also overheating of the area of the body surface on which the breast prosthesis lies. This is perceived as unpleasant by the users. Furthermore, irritation of the skin can occur, which is likewise undesirable.

A proposal for the elimination of the aforesaid problems comprises forming the side of the breast prosthesis facing the body as a latent heat store by means of which excess heat should be eliminated. The latent heat store is made over the full area in breast prostheses correspondingly present on the market.

SUMMARY OF THE INVENTION

It is now the object of the present invention to further develop a breast prosthesis of the initially named type in an advantageous manner, in particular such that it provides more comfort in wear and avoids irritation of the skin.

This object is achieved in accordance with the invention by a breast prosthesis having the features herein. Provision is accordingly made that a breast prosthesis has at least one contact surface which is intended for contact on a body surface, with the contact surface having at least one means by means of which air circulation and/or an exchange of air can be achieved between the contact surface and the body surface.

The advantage thereby results that air circulation and/or an exchange of air is/are ensured between the contact surface and the body surface in wear, but also that the contact surface of the breast prosthesis on the body surface is reduced. The comfort in wear can thereby be considerably increased. An overheating and thus also perspiration can furthermore be avoided due to the air circulation and/or the exchange of air. The air cushion forming between the contact surface and the body surface moreover improves the microclimate in this area.

Provision can furthermore be made that the means includes one or more moldings and/or that the means is formed as at least one molding, with the at least one molding rising at least partly out of the contact surface and/or being recessed therein.

It is furthermore possible that the molding rises at least toward a rim of the contact surface, preferably in each case toward all rims of the contact surface, in a reducing manner with respect to the height from the contact surface and/or is lowered therein in a reducing manner with respect to the depth. The advantage hereby results that the transition can be achieved at the rims of the breast prostheses to the body of the woman. This advantageously increases the comfort in wear and furthermore produces a visually pleasing impression.

It is furthermore conceivable that the means is and/or comprises at least one nub, with the nub or nubs preferably being formed in an elliptic and/or round manner and/or in tear-form.

A forming of the nubs can take place, for example, in that a nub cavity or mold is provided for the molding of the prosthesis blank with or without vacuum in the manufacturing process. It is furthermore conceivable to provide a separate mold, for instance a nub shell, which can be placed onto already used cavities or molds (cosmetic layer membrane cavity/pattern). It is conceivable to use 3D injection molding for the manufacture or to apply the nub mold parts individually.

It is equally conceivable that the nubs can be subsequently applied to a standard blank for a breast prosthesis, for instance by bead application. It is furthermore possible to foam the nubs on, for instance by integral foam and/or thermoplastic foam.

It is also feasible to apply DU Expancel paste onto the standard blank and to activate it thermally, for instance in the manner of T-shirt printing or to arrange DU Expancel in the rear side of the silicone and to activate it partially thermally. The thermal activation can be achieved by infrared, radio frequency, heating patterns or lasers.

A further possibility comprises to mill the nubs out of a hard rear side, that is, for instance, to provide a hard silicone plate for the contact surface from which the nubs and the contact surface are shaped, in particular milled out.

Provision can be made that the size of the nubs reduces at least toward one rim, preferably in each case toward all rims, and is preferably the largest in the middle area of the contact surface.

It is furthermore possible that a plurality of means, preferably nubs, are present which are arranged on the contact surface such that at least one air passage by means of which air can be led in and out is formed by the arrangement on the body surface in the applied state.

Provision can furthermore be made that air can be led in and out through the air passage by a chimney effect and/or by pump pressure or pressing in at least a part of the breast prosthesis. The advantage thereby results of being able actively to support air circulation and/or an exchange of air.

It is moreover conceivable that the breast prosthesis has at least one latent heat store or at least partly comprises latent heat store material, with the latent heat store or the latent heat store material preferably being PCM material. Material is preferably used as the latent heat store or as the latent heat material whose melting point is in the region of body temperature so that excess heat energy is absorbed by the phase transition which occurs from the solid to the liquid phase of the latent heat store or of the latent heat store material.

It is furthermore possible that the latent heat store or the latent heat store material is arranged in the region of the contact surface.

Provision can advantageously be made that the latent heat store or the latent heat store material is arranged in the region of the means. An optimization of the effect of the PCM material can in particular be achieved by the nub structure in combination with a PCM material in that areas with skin contact react fast, further areas in the nub center start later through heat conduction and the areas at the nub tip react more long-lastingly via air circulation. A buffer effect can thus advantageously be achieved. The effect of the PCM material can furthermore be developed more or exploited better due to the enlarged surface. A considerably improved comfort in wear, a prevention of overheating and an improvement in the microclimate can advantageously be achieved.

It is furthermore conceivable that the means, in particular the nubs, is/are formed at least partly by the latent heat store or the latent heat store material and/or at least partly comprises/comprise the latent heat store or the latent heat store material.

It is furthermore possible that the breast prosthesis at least partly consists of an addition curing two-component silicone rubber compound or comprises an addition curing two-component silicone rubber compound.

Provision can furthermore be made that the breast prosthesis is formed from at least one compound welded into plastic film and/or simulates the shape of the breast, with the compound preferably at least partly comprising an addition-curing two-component silicone rubber compound and/or that the breast prosthesis comprises a shell-shaped body of a soft elastically set plastic, preferably an addition cured two-component silicone rubber compound which is welded into plastic films and thus forms a first chamber and comprises a second chamber facing the wearer during wear, adjoining the first chamber and fillable with a filler material. Polyurethane films can be used as plastic films, for example.

It is moreover conceivable that the molding is formed by a compound welded into plastic film, with the compound preferably at least partly comprising an addition curing two-component silicone rubber compound.

Provision can furthermore be made that the breast prosthesis and/or the at least one means is formed at least partly from foam. It is, for example, conceivable that the nubs are made from foam. It is also possible that foam beads rise from the contact surface.

BRIEF DESCRIPTION OF THE DRAWINGS

Further details and advantages of the invention will now be explained in more detail with reference to an embodiment shown in the drawing.

There are shown.

DESCRIPTION OF THE PREFERRED EMBODIMENTS

Figure 1:
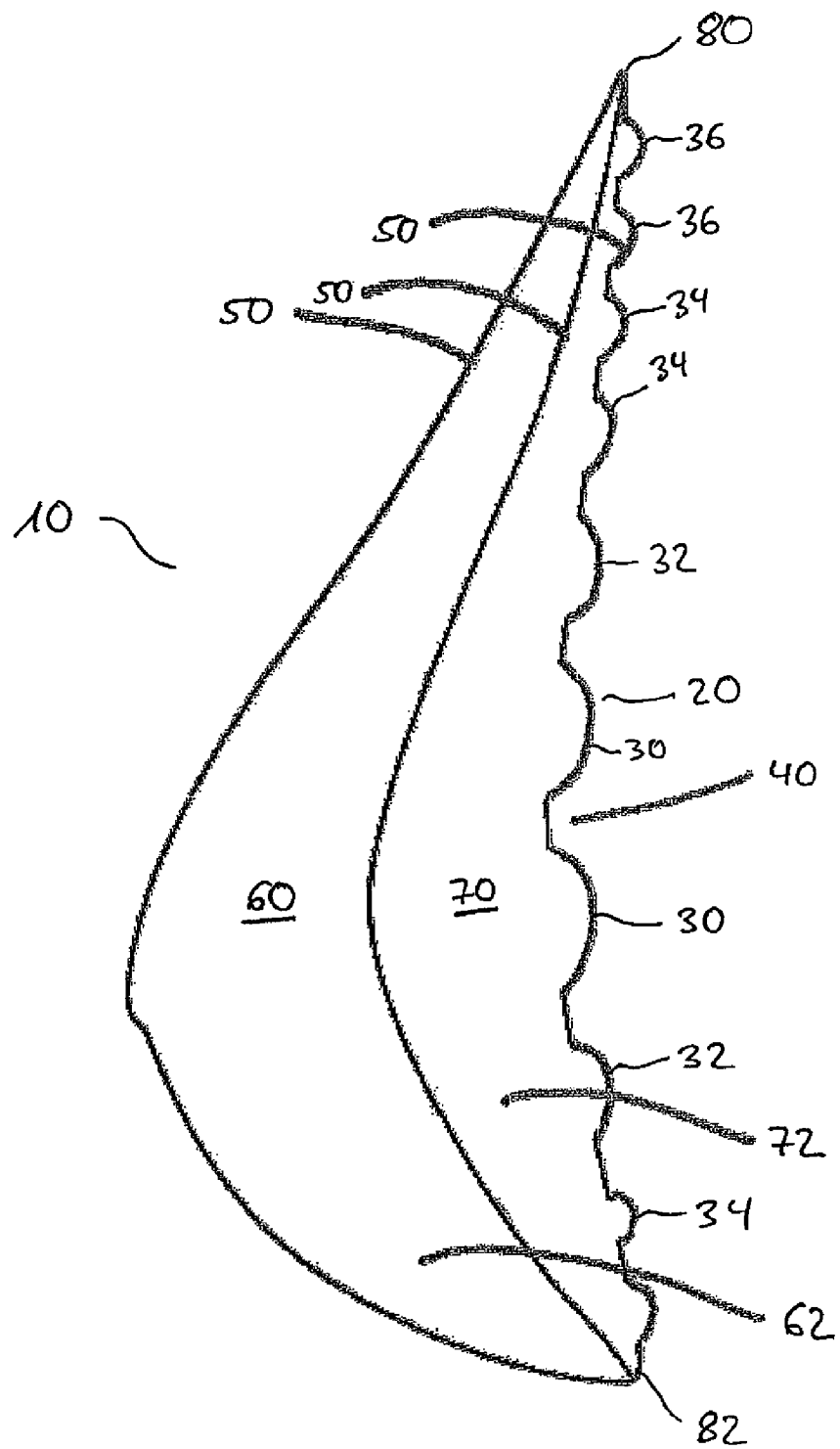
FIG. 1: a sectional representation of the breast prosthesis in a first embodiment in a side view.

FIG. 1 shows a sectional representation of the breast prosthesis 10 in a first embodiment in a side view. The breast prosthesis 10 is in this respect based on the shape of a female breast and can be designed as a right breast prosthesis or as a left breast prosthesis. It is equally conceivable that a single embodiment of the breast prosthesis 10 is provided for the right hand side or for the left hand side. The breast prosthesis 10 is in this respect triangular in a frontal view and has convex outer edges or rims 80, 82, 84.

The breast prosthesis 10 has two chambers 60 and 70, with the first chamber 60 being outwardly disposed or remote from the contact surface 20 and being formed or bounded by two films 50. The films 50 are polyurethane films 50. The chamber 60 is filled with an addition curing two-component silicone rubber compound 62.

The second chamber 70 is inwardly disposed, i.e. an outer surface 20 of the chamber 70 is a contact surface 20 which is provided for the contact on the body surface. The chamber 70 is likewise bounded by two films 50, with the film 50 disposed in the interior of the breast prosthesis 10 separating the chambers 60 and 70 from one another. The chamber 70 is in this respect preferably filled with latent heat store material 72, in particular PCM material 72.

The means 30, 32, 34, 36 by means of which air circulation and an exchange of air can be achieved between the contact surface 20 and the body surface (not shown in FIG. 1) rise from the contact surface 20. The means 30, 32, 34, 36 are in this respect designed as nubs 30, 32, 34, 36 which rise from the contact surface 20 so that air guidance passages 40 are formed between the nubs 30, 32, 34, 36 which enable air circulation between the contact surface 20 and the body surface.

The nubs 30, 32, 34, 36 are in this respect formed by the shape of the chamber 70, for instance by the shape of the latent heat store material 72 surrounded by the film 50. Provision can, however, equally be made that the nubs 30, 32, 34, 36 are set separately onto the contact surface 20 or onto the film 50.

The height and also the size of the nubs 30, 32, 34, 36 each reduces toward the rims 80, 82, that is, toward the upper rim 80 and the lower rim 82 of the contact surface 20, preferably also toward the side rims 84 of the contact surface 20 not shown in FIG. 1. The nubs 30, 32, 34, 36 are preferably made circular with respect to the cross-section and rise semi-spherically from the contact surface 20.

The nubs 30 in the first and largest height and size are in this respect arranged at the center of the contact surface 20 and are surrounded by the nubs 32 in the second and next smaller size and height. The nubs 34 and 36 follow thereupon reducing in the third and fourth height and size, respectively reducing. The advantage thereby results that the breast prosthesis can contact the body of the woman better at the edges 80, 82, which furthermore has an improved visual effect in addition to a pleasant feeling in wear.

The air circulation and the exchange of air between the contact surface 20 of the breast prosthesis 10 and the body surface, not shown, already takes place without any further assistance through the chimney effect so that the warm air draws off and environmental air flows in. The microclimate is thereby considerably improved over previous approaches.

Provision can alternatively or additionally be made that the air circulation and the exchange of air between the contact surface 20 of the breast prosthesis 10 and the body surface, not shown, is actively supported by pressing in the breast prosthesis 10 since the air present between the contact surface 20 of the breast prosthesis 10 and the body surface is hereby pumped out and environmental air is sucked into the intermediate spaces 40 or air passages 40.

Figure 2:
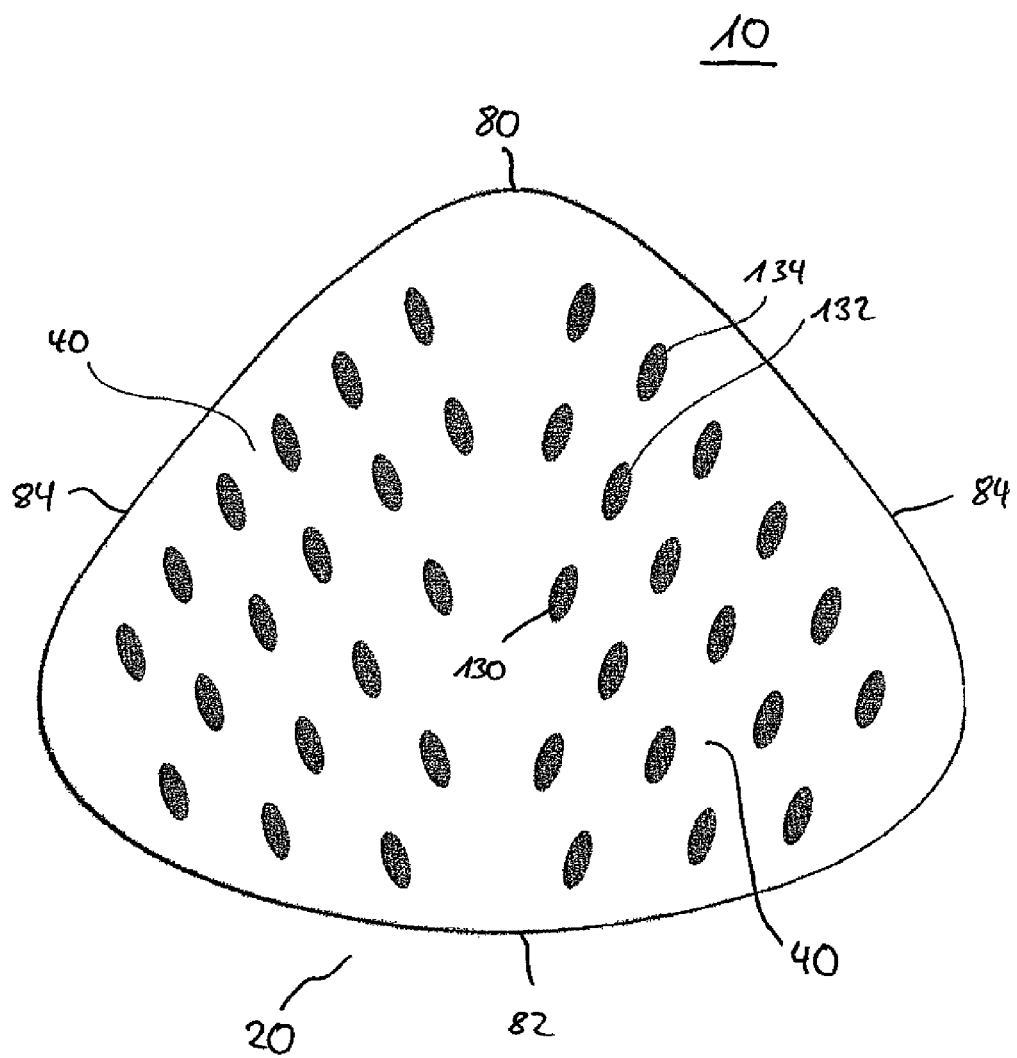
FIG. 2: a rear view of the breast prosthesis in a further embodiment.

FIG. 2 shows a rear view of a further embodiment of the breast prosthesis 10 with a view of the contact surface 20. A plurality of oval or elliptical nubs 130, 132, 134 which rise from the contact surface 20 at different heights and between which intermediate spaces 40 are present which serve the air circulation and the exchange of air. In this respect, the height of the nubs 130, 132, 134 in each case reduces toward the rims 80, 82, 84, that is, toward the upper rim 80 and the lower rim 82 as well as toward the side rims 84 of the contact surface 20.

Figure 3:
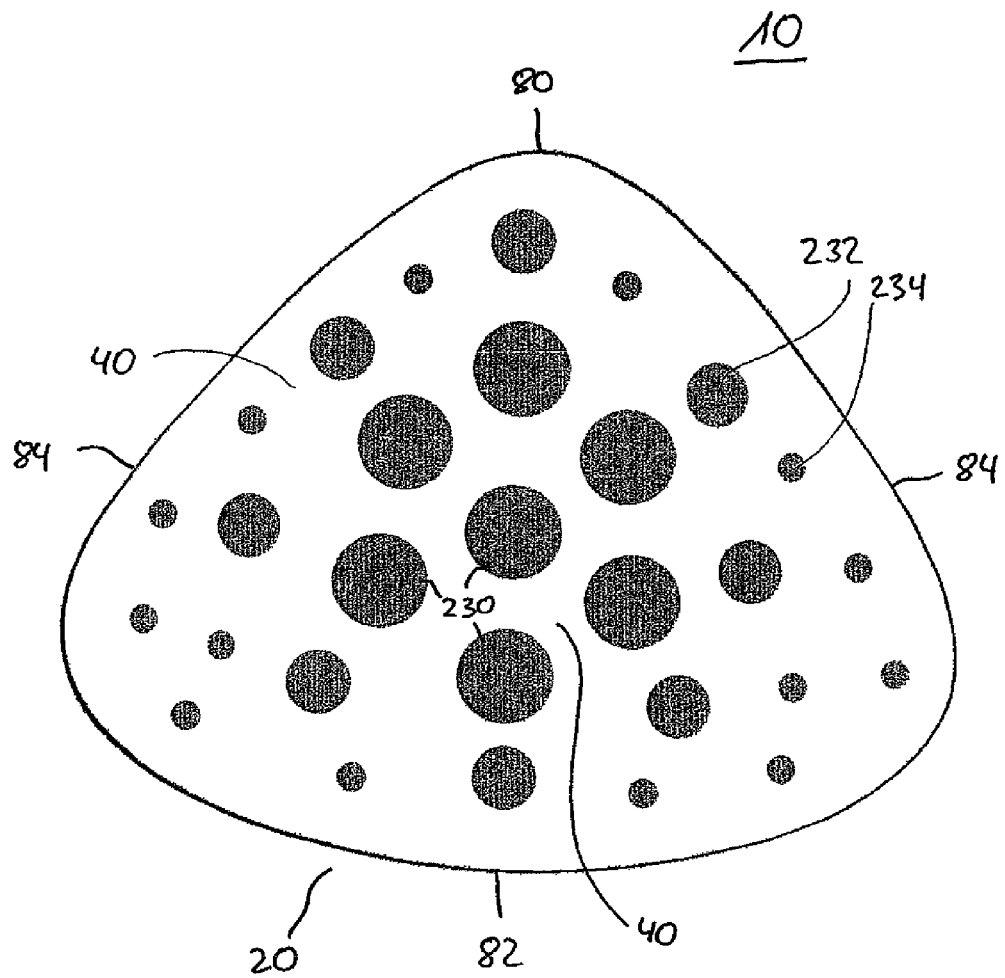
FIG. 3: a rear view of the breast prosthesis in a further embodiment.

FIG. 3 shows a rear view of a further embodiment of the breast prosthesis 10 with a view of the contact surface 20. A plurality of circular nubs 230, 232, 234 which rise from the contact surface 20 in a plurality of heights and sizes and in an approximately semi-spherical shape and between which intermediate spaces are present which serve the air circulation and the exchange of air rise from the contact surface 20. In this respect, the height and size of the nubs 230, 232, 234 in each case reduce toward the rims 80, 82, 84, that is, toward the upper rim 80 and the lower rim 82 as well as toward the side rims 84 of the contact surface 20.

Figure 4:
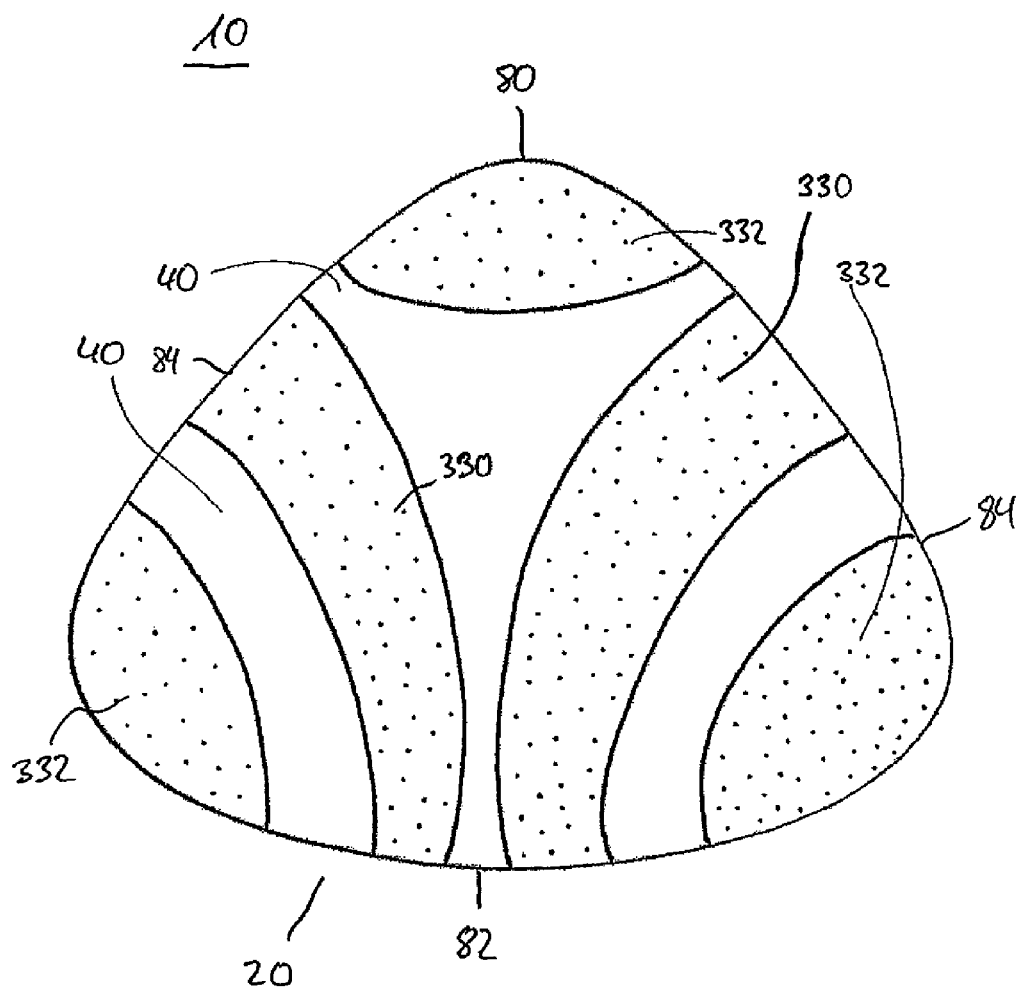
FIG. 4: a rear view of the breast prosthesis in a further embodiment.

FIG. 4 shows a rear view of a further embodiment of the breast prosthesis 10 with a view of the contact surface 20, with the means 330, 332 for the achievement of an exchange of air between the contact surface 20 and the body surface are made as foam moldings 330, 332. The moldings 330, 332 in this respect rise from the contact surface 20, with the moldings 332 disposed at the side rims 80, 82, 84 or in the corner regions having a lower height than the moldings 330 which are arranged centrally in the contact surface 20. The bead-shaped moldings 330, however, likewise reduce in height in the areas disposed adjacent to the rims 82, 82. Intermediate spaces 40 or air passages 40 through which an exchange of air is enabled are located between the moldings 330, 332. An approximately triangular intermediate space 40 which has concave sides is formed between the two moldings 330 and the molding 33 located in the upper corner 80.

The invention claimed is:

1. A breast prosthesis (10) having at least one contact surface (20) which is intended for the contact on a body surface, wherein
the contact surface (20) has means (30, 32, 34, 36, 130, 132, 134, 230, 232, 234) by which air circulation and/or an exchange of air can be achieved between the contact surface (20) and the body surface and which comprise a series of raised nubs (30, 32, 34, 36, 130, 132, 134, 230, 232, 234) defining air guidance passages (40) therebetween,
size or height of said individual nubs (30, 32, 34, 36, 130, 132, 134, 230, 232, 234) reducing towards all rims (80, 82, 84) of said contact surface (20) and being largest in a middle or center area of said contact surface (20).

2. A breast prosthesis (10) having at least one contact surface (20) which is intended for the contact on a body surface, wherein
the contact surface (20) has means (330, 332) by which air circulation and/or an exchange of air can be achieved between the contact surface (20) and the body surface and which comprise a series of moldings defining air guidance passages (40) therebetween,
with the moldings (330, 332) each extending across the contact surface (20) from rims (80, 82, 84) thereof and being of variable height.

3. A breast prosthesis (10) in accordance with claim 2, wherein the molding rises at least toward one rim (80, 82, 84) of the contact surface (20), preferably in each case toward all rims (80, 82, 84) of the contact surface (20) in a reducing manner with respect to the height from the contact surface (20) and/or is lowered therein in a reducing manner with respect to the depth.

4. A breast prosthesis (10) in accordance with claim 1, wherein the nubs (30, 32, 34, 36, 130, 132, 134, 230, 232, 234) are formed in elliptic or round manner and/or in tear form.

5. A breast prosthesis (10) in accordance with claim 1, wherein air can be led in and out through the air passage (40) by the chimney effect and/or by pump pressure or pressing in at least a part of the breast prosthesis (10).

6. A breast prosthesis in accordance with claim 1, wherein the breast prosthesis (10) has at least one latent heat store (72) or at least partly comprises latent heat store material (72), with the latent heat store (72) or the latent heat store material (72) preferably being PCM material.

7. A breast prosthesis (10) in accordance with claim 6, wherein the latent heat store (72) or the latent heat store material (72) is arranged in the region of the contact surface (20).

8. A breast prosthesis (10) in accordance with claim 6, wherein the latent heat store (72) or the latent heat store material (72) is arranged in the region of the means (30, 32, 34, 36, 130, 132, 134, 230, 232, 234, 330, 332).

9. A breast prosthesis (10) in accordance with claim 6, wherein the nubs (30, 32, 34, 36, 130, 132, 134, 230, 232, 234) at least partly comprise the latent heat store (72) or the latent heat store material (72).

10. A breast prosthesis (10) in accordance with claim 1, wherein the breast prosthesis (10) at least partly consists of an addition-curing two-component silicone rubber compound (62) or comprises an addition curing two-component silicone rubber compound (62).

11. A breast prosthesis (10) in accordance with claim 1, wherein the breast prosthesis (10) is formed from at least one compound (62, 72) welded into plastic film (50) and/or simulates the shape of the breast, with the compound (62, 72) preferably at least partly comprising an addition-curing two-component silicone rubber compound (62); and/or the breast prosthesis (10) comprises a shell-shaped body of a soft elastically set plastic, preferably an addition cured two-component silicone rubber compound (62) which is welded into plastic films (50) and thus forms a first chamber (60) and comprises a second chamber (70) facing the wearer during wear, adjoining the first chamber (60) and fillable with a filler material (72).

12. A breast prosthesis (10) in accordance with claim 11, wherein the molding is formed by compound (62, 72) welded into plastic film (50), with the compound (62, 72) preferably at least partly comprising an addition curing two-component silicone rubber compound (62).

13. A breast prosthesis (10) in accordance with claim 1, wherein the breast prosthesis (10) and/or the at least one means (30, 32, 34, 36, 130, 132, 134, 230, 232, 234, 330, 332) is made at least partly from foam.

14. A breast prosthesis (10) in accordance with claim 2, wherein the breast prosthesis (10) is formed from at least one compound (62, 72) welded into plastic film (50) and/or simulates the shape of the breast, with the compound (62, 72) preferably at least partly comprising an addition-curing two-component silicone rubber compound (62); and/or the breast prosthesis (10) comprises a shell-shaped body of a soft elastically set plastic, preferably an addition cured two-component silicone rubber compound (62) which is welded into plastic films (50) and thus forms a first chamber (60) and comprises a second chamber (70) facing the wearer during wear, adjoining the first chamber (60) and fillable with a filler material (72).

15. A breast prosthesis (10) in accordance with claim 14, wherein the molding is formed by compound (62, 72) welded into plastic film (50), with the compound (62, 72) preferably at least partly comprising an addition curing two-component silicone rubber compound (62).

16. A breast prosthesis (10) in accordance with claim 2, wherein side moldings (332) adjacent the rims (80, 82, 84) have lower height than centrally-disposed moldings (330).

17. A breast prosthesis (10) according to claim 16, wherein the centrally-disposed moldings (330) decrease in height towards the rims (80, 82, 84).

18. A breast prosthesis (10) according to claim 17, wherein an approximately triangular intermediate space (40) having concave sides is formed between the centrally-disposed moldings (330) and one of the side moldings (332) and defining an air guidance passage (40).

19. A breast prosthesis (10) according to claim 16, wherein an approximately triangular intermediate space (40) having concave sides is formed between the centrally-disposed moldings (330) and one of the side moldings (332) and defining an air guidance passage (40).

* * * * *